United States Patent
Hao

(10) Patent No.: US 8,044,093 B2
(45) Date of Patent: Oct. 25, 2011

(54) PHARMACEUTICAL COMPOSITIONS COMPRISING DOCETAXEL AND METHODS FOR PREPARATION THEREOF

(75) Inventor: Shouzhu Hao, Beijing (CN)

(73) Assignee: Beijing Century Biocom Pharmaceutical Technology Co., Ltd., Beijing (CN)

( * ) Notice: Subject to any disclaimer, the term of this patent is extended or adjusted under 35 U.S.C. 154(b) by 0 days.

(21) Appl. No.: 12/194,609

(22) Filed: Aug. 20, 2008

(65) Prior Publication Data

US 2008/0306137 A1   Dec. 11, 2008

Related U.S. Application Data

(63) Continuation of application No. PCT/CN2007/000527, filed on Feb. 14, 2007.

(30) Foreign Application Priority Data

Feb. 20, 2006   (CN) .......................... 2006 1 0008101

(51) Int. Cl.
    *A61K 31/335*   (2006.01)
(52) U.S. Cl. ..................................... 514/449
(58) Field of Classification Search ................... 514/449
    See application file for complete search history.

(56) References Cited

U.S. PATENT DOCUMENTS

| 5,698,582 | A  | * | 12/1997 | Bastart et al. ............. 514/449 |
| 6,251,428 | B1 | * | 6/2001  | Yoo .......................... 424/455 |
| 6,388,112 | B1 | * | 5/2002  | Anevski ..................... 554/191 |
| 6,828,346 | B2 | * | 12/2004 | Joshi-Hangal et al. ........ 514/449 |
| 2003/0077297 | A1 | * | 4/2003 | Chen et al. ................. 424/400 |
| 2003/0207936 | A1 | * | 11/2003 | Chen ....................... 514/449 |

FOREIGN PATENT DOCUMENTS

| WO | WO 97/23208  | * | 7/1997  |
| WO | WO 2006/133510 | * | 12/2006 |

OTHER PUBLICATIONS

Chen et al. Pharmaceutical Research, Aug. 2003, vol. 20, No. 8, pp. 1302-1308.*

* cited by examiner

*Primary Examiner* — James Anderson
(74) *Attorney, Agent, or Firm* — Matthias Scholl P.C.; Matthias Scholl

(57) ABSTRACT

A pharmaceutical composition of docetaxel comprising an effective amount of docetaxel, a polysorbate (TWEEN® compound) and a co-solvent, wherein the co-solvent is at least one member selected from the group consisting of glycerol and polyethylene glycol. The composition is an injectable solution or a freeze-dried powder for injection. The solubility of decetaxel is improved by adding a polysorbate and a co-solvent. Methods of preparation of the pharmaceutical composition are also disclosed.

22 Claims, No Drawings

PHARMACEUTICAL COMPOSITIONS COMPRISING DOCETAXEL AND METHODS FOR PREPARATION THEREOF

CROSS-REFERENCE TO RELATED APPLICATIONS

This application is a continuation of International Patent Application No. PCT/CN2007/000527 with an international filing date of Feb. 14, 2007, designating the United States, now pending, and further claims priority benefits to Chinese Patent Application No. 200610008101.9 filed Feb. 20, 2006. The contents of all of the aforementioned applications, including any intervening amendments thereto, are incorporated herein by reference.

BACKGROUND OF THE INVENTION

1. Field of the Invention

This invention relates to a pharmaceutical composition comprising docetaxel, methods for producing the same, and methods for using the composition.

2. Description of the Related Art

Taxanes are a class of potent anti-tumor agents. The mechanism of their action comprises binding to microtubules to promote and stabilize microtubule assembly, and further to prevent physiological microtubule depolymerisation and disassembly. This leads to a significant decrease in free tubulin, results in inhibition of mitotic cell division and apoptosis of the cancer cell.

Currently, the most widely used taxanes are paclitaxel and docetaxel, which have been approved for the treatment of primary and metastatic cancer comprising breast cancer, ovarian cancer, non-small cell lung cancer (NSCLC), small cell lung cancer (SCLC), head and neck squamous cell carcinoma, and malignant melanoma.

However, taxanes, and in particular paclitaxel and docetaxel, have very poor solubility in aqueous solutions. Thus, formulating these compounds is difficult. For example, commercially available docetaxel (Taxotere) is formulated in a highly concentrated solution containing 40 mg docetaxel and 1040 mg TWEEN® 80 (polysorbate 80) per mL. This concentrated solution has to be diluted with solvent containing 13% ethanol in saline before administration.

Although a number of methods have been reported in the literature that claim improved formulation and solubility of taxanes, these methods are based on the formation of emulsion, or microemulsion, or on the inclusion of cyclodextrins, liposomes, nanoparticles, etc. However, each of above methods is hampered by one or more problems, such as complicated preparation, high cost, and low stability of the formulations. Therefore, there is an urgent need for a pharmaceutical composition comprising taxanes, the composition having high solubility and stability, simplified preparation process, and exhibiting lower hypersensitivity in patients.

SUMMARY OF THE INVENTION

In view of the above-described problems, it is one objective of the invention to provide a pharmaceutical composition of taxanes, the composition having high solubility and stability, simplified preparation process, and exhibiting lower hypersensitivity in patients.

To achieve the above objectives, in accordance with one embodiment of the invention, provided is a pharmaceutical composition comprising an efficacious dosage of taxane (such as docetaxel), TWEEN® surfactant and one or more solubilizing agents, such as glycerol or polyethylene glycol.

The surfactant employed in the composition of this invention is selected from TWEEN® 20, TWEEN® 40, TWEEN® 60, TWEEN® 80, or a mixture thereof, and is preferably TWEEN® 80.

The solubilizing agent employed in the composition of this invention is glycerin, polyethylene glycol, or a mixture thereof. The average molecular weight of polyethylene glycol is 200-10000. PEG200, PEG400, PEG800 are preferred.

In the docetaxel composition of this invention, the weight ratio of taxane (such as docetaxel) to TWEEN® surfactant to solubilizing agent is 1:5-150:2-100. The preferred weight ratio of taxane (such as docetaxel) to TWEEN® surfactant to solubilizing agent is 1:10-80:5-50, and the most preferred weight ratio of taxane (such as docetaxel) to TWEEN® surfactant to solubilizing agent is 1:25-40:10-30.

The docetaxel composition in this invention is suitable for parenteral administration, and is provided in the form of injection solution or lyophilized powder form. The concentration of taxane in the injection solution or in the solution before freeze-drying is between 0.1 mg/mL and 80 mg/mL, preferably between 1 mg/mL and 80 mg/mL. The concentration of solubilizing agent is between 5 mg/mL and 500 mg/mL, preferably between 30 mg/mL and 200 mg/mL. The concentration of TWEEN® surfactant of the solution is between 20 mg/mL and 500 mg/mL, and preferably between 30 mg/mL and 300 mg/mL.

The docetaxel composition described in this invention also comprises other agents and additives that are commonly used in injection solution or preparations for freeze-dried powder. These agents or the additives include, but are not limited to, freeze-drying excipients, preservatives, stabilizers, pH regulators, and isotonic sterile injection solutions.

Examples of suitable excipients are selected from, but are not limited to, one or more of mannitol, lactose, glucose, sorbitol, sodium chloride, hydrolyzed gelatin, dextran, sucrose, glycine, polyvinylpyrrolidone (PVP); and preferably glucose or mannitol.

Examples of suitable preservatives are selected from, but are not limited to, one or more of phenol, cresol, butyl alcohol, benzyl alcohol and nipagin.

Examples of suitable stabilizers are selected from, but are not limited to, one or more of sodium sulfite, sodium bisulfite, sodium metabisulfite, sodium thiosulfate, thiourea, Vitamin C, 3-tert-butyl-4-hydroxyanisole (BHA), dibutylphenol, propyl gallate, tocopherol, methionine, cysteine hydrochloride, acetylcysteine, N-acetyl-DL-methionine, ascorbyl palmitate, EDTA, EDTA disodium salt.

Examples of pH regulators are selected from, but are not limited to, one or more of hydrochloric acid, citric acid, tartaric acid, phosphoric acid, metaphosphoric acid, polymetaphosphoric acid, carbonic acid, sodium hydroxide, potassium hydroxide, sodium citrate, potassium citrate, sodium bicarbonate, potassium bicarbonate, ammonium carbonate, sodium hydrogen phosphate, potassium hydrogen phosphate, ethanolamine, diethanolamine, triethanolamine, hexane-1,2-diamine, sodium carbonate, sodium potassium tartrate, potassium metaphosphate, potassium polymetaphosphate, and sodium metaphosphate.

Preferably, the pH value of docetaxel solution of this invention is less than 8, more preferably in the range of between 3 and 5. Preferably, the pH regulators are selected from, but are not limited to, one or more of hydrochloric acid, citric acid, tartaric acid, phosphoric acid, metaphosphoric acid, or polymetaphosphoric acid; and more preferably citric acid, or tartaric acid.

The docetaxel composition in this invention can further comprise bile acid or salt thereof, which increases the stability of the composition. The bile acid is selected from free bile acids, conjugated bile acids, or a mixture of both. Suitable free bile acids include cholic acid, lithocholic acid, deoxycholic acid, chenodeoxycholic acid, ursodeoxycholic acid, hyodeoxycholic acid, etc, and are preferably cholic acid, deoxycholic acid, chenodeoxycholic acid, or hyodeoxycholic acid. Suitable conjugated bile acids are selected from amides, which are the products of a chemical reaction of the above free bile acid with glycine ($H_2NCH_2COOH$), taurine ($H_2NCH_2CH_2SO_3H$) or other compounds having an amino group. Preferred conjugated bile acids are glycocholic acid, glycodeoxycholic acid, glycochenodeoxycholic acid, glycoursodeoxycholic acid, taurocholic acid, taurodeoxycholic acid, taurochenodeoxycholic acid, or tauroursodeoxycholic acid. Bile acid salts refer to salts of free bile acids or conjugated bile acids. Bile acid salts include, but not limited to, potassium salts, sodium salts, calcium salts, magnesium salts, zinc salts, selenium salts, iron salts, etc. Preferred bile acid salts are sodium or potassium salts of bile acids.

This invention places no special restriction on the amount of docetaxel contained in the composition. Doctors can adjust the amount of docetaxel to the efficacious dose based on the patient's need for effective treatment. In general, the content of docetaxel in the composition described in this invention is between 0.1 and 80 mg/mL.

The docetaxel composition of this invention can be prepared in the forms of either a clear injection solution or a freeze-dried powder that can be reconstituted into clear injection solution by dissolving the powder in 5% sterile water, 10% glucose solution, or 0.9% sodium chloride aqueous solution.

Advantages of the invention include:
1) The docetaxel pharmaceutical composition does not require a special solvent, thus simplifying preparation, and is less allergenic.
2) The composition can be lyophilized into powder or solid chunks, which can reduce or prevent docetaxel from oxidation and hydrolysis. A solid form does not only make the drug more stable but is also more convenient for transportation;
3) The injection powder is simpler to produce and easier to control in terms of quality. The product has good stability and is suitable for large-scale manufacturing.
4) The composition has relatively high melting point. Pre-frozen temperature can be as high as −40° C. for lyophilization. The water content of the composition can reach 1% or less after the freeze-dried process. Typically, the water content of the composition is controlled at less than 5%.

Turbidity of the injection solution described in this invention was measured following the procedures published in "Chinese Pharmacopoeia 2005 (2)" Appendix IX B. The procedure involves visual comparison of the sample solution with a standard reference solution. Both sample solution and standard solutions were freshly prepared and placed in Nessler tubes in equal volumes. The solutions were allowed to stand for 5 min before the measurement. The tubes were placed vertically in a dark room under an umbrella light having a light intensity of 1000 Lux. Turbidity was observed from the side and the solution described in this invention was less turbid than that of the reference solution of scale No. 1, rated "clear".

The injection solution or freeze-dried powder of the pharmaceutical composition comprising a taxane, such as docetaxel, described herein, is suitable for intramuscular and intravenous injection.

This invention provides a method of improving docetaxel solubility and preparing a pharmaceutical composition of docetaxel, the method comprising: mixing docetaxel with a solubilizing agent and TWEEN® surfactant. It also provides additional method for converting the composition into an injection solution comprising: (a) mixing with aqueous solvent such as mannitol solution or solution containing suitable additives followed by addition of activated carbon; and (b) after stirring, filtering the mixture through a 0.8 μm membrane to remove the carbon and filtering the filtrate again through a 0.2 μm membrane to remove microbes. The solution was then ready for packaging. The final injection solution should contain between 5 mg/mL and 500 mg/mL of solubilizing agent and between 20 mg/mL and 500 mg/mL of TWEEN® or other surfactant. This invention also provides procedures of preparing injection powder from the injection solution described above using standard lyophilization techniques that is commonly used in the pharmaceutical industry.

In a class of this embodiment, the method provided herein comprises mixing docetaxel with one or more surfactants, one or more solubilizing agents and one or more additives, and then adding aqueous media, and stirring until clear solution is obtained.

In another class of this embodiment or in another embodiment, the weight ratio of docetaxel to surfactant and solubilizing agent is 1:5-150:2-100; preferably 1:10-80:5-50; and more preferably 1:25-40:10-30.

The third aspect of this invention involves using the composition of present invention for treating proliferative diseases, and in particular cancers. Examples of cancers that can be treated by the composition described herein include breast cancer, non-small cell lung cancer, ovarian cancer, AIDS-related Kaposi's sarcoma, pancreatic cancer, colorectal cancer, melanoma, head and neck cancer, lymphoma, brain tumor, gastric cancer, stomach cancer etc.

To those skilled in the art, it is apparent that several variations are possible within the scope and spirit of this invention. The following examples and illustrations are provided only for the purposes of clarity of understanding. Therefore, the description and examples below should not be construed as limiting the scope of the invention and certain minor changes and modifications apparently based on this invention should be covered by this invention.

DETAILED DESCRIPTION OF THE INVENTION

EXAMPLE 1

| | |
|---|---|
| Docetaxel | 20 mg |
| Polyethylene glycol 200 | 200 mg |
| TWEEN ® 80 | 500 mg |
| Mannitol | 300 mg |
| WFI water (water for injection quality) | Add to 3 mL total volume |

To a mixture of docetaxel, polyethylene glycol 200 and TWEEN® 80 added was mannitol aqueous solution. The pH value of the mixture was adjusted to 4 using citric acid followed by addition of activated carbon (0.1%). The mixture was stirred for 20 min and filtered through a 0.8 μm membrane to remove carbon. The filtrate was filtered again through a 0.22 μm membrane for removing microbes.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically in a dark room under umbrella light with light intensity of 1000 Lux. Turbidity was observed from the side and the sample solution described in this example is less turbid than that of the reference solution of scale No. 1, rated "clear".

EXAMPLE 2

| Docetaxel | 20 mg |
| Polyethylene glycol 400 | 350 mg |
| TWEEN ® 80 | 800 mg |
| Mannitol | 450 mg |
| WFI water | Add to 5 mL total volume |

To a mixture of docetaxel, polyethylene glycol 200 and TWEEN® 80 added was mannitol aqueous solution. The pH value of the mixture was adjusted to 4 using tartaric acid followed by addition of activated carbon (0.1%). The mixture was stirred for 20 min and filtered through a 0.8 μm membrane to remove carbon. The filtrate was filtered again through a 0.22 μm membrane to remove microbes.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 3

| Docetaxel | 20 mg |
| Polyethylene glycol 400 | 300 mg |
| TWEEN ® 80 | 800 mg |
| Mannitol | 500 mg |
| WFI water | Add to 6 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 4

| Docetaxel | 20 mg |
| Glycerol | 150 mg |
| Polyethylene glycol 400 | 200 mg |
| TWEEN ® 80 | 600 mg |
| Mannitol | 400 mg |
| WFI water | Add to 6 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 5

| Docetaxel | 20 mg |
| Glycerol | 150 mg |
| TWEEN ® 80 | 1600 mg |
| Mannitol | 300 mg |
| WFI water | Add to 3 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 6

| Docetaxel | 40 mg |
| Glycerol | 600 mg |
| TWEEN ® 80 | 1600 mg |
| Mannitol | 600 mg |
| WFI water | Add to 10 mL total volume |

The injection solution of this example was prepared using the procedure described in example 1. The amounts and compounds used were as in the table above.

Turbidity of the injection solution was measured following the procedures published in "Chinese Pharmacopoeia 2005

(2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 7

| | |
|---|---|
| Docetaxel | 20 mg |
| Glycerol | 350 mg |
| TWEEN ® 80 | 650 mg |
| Mannitol | 500 mg |
| WFI water | Add to 5 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 8

| | |
|---|---|
| Docetaxe | 40 mg |
| Glycerol | 300 mg |
| Polyethylene glycol 400 | 200 mg |
| TWEEN ® 80 | 3200 mg |
| Mannitol | 600 mg |
| WFI water | Add to 7 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 9

| | |
|---|---|
| Docetaxel | 20 mg |
| Glycerol | 350 mg |
| TWEEN ® 20 | 3000 mg |
| Mannitol | 200 mg |
| WFI water | Add to 10 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 10

| | |
|---|---|
| Docetaxel | 20 mg |
| Glycerol | 350 mg |
| TWEEN ® 40 | 800 mg |
| Mannitol | 400 mg |
| WFI water | Add to 5 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 11

| | |
|---|---|
| Docetaxel | 20 mg |
| Polyethylene glycol 400 | 350 mg |
| TWEEN ® 60 | 800 mg |
| Mannitol | 400 mg |
| WFI water | Add to 5 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 12

| | |
|---|---|
| Docetaxel | 20 mg |
| Polyethylene glycol 400 | 200 mg |
| TWEEN ® 80 | 600 mg |
| Cholic acid | 50 mg |
| Mannitol | 500 mg |
| WFI water | Add to 5 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 13

| | |
|---|---|
| Docetaxel | 20 mg |
| Glycerol | 100 mg |
| Polyethylene glycol 400 | 250 mg |
| TWEEN ® 80 | 300 mg |
| Glycocholic acid | 200 mg |
| Mannitol | 300 mg |
| WFI water | Add to 5 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 14

| | |
|---|---|
| Docetaxel | 20 mg |
| Glycerol | 250 mg |
| TWEEN ® 80 | 800 mg |
| Taurocholic acid | 150 mg |
| Mannitol | 250 mg |
| WFI water | Add to 5 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 15

| | |
|---|---|
| Docetaxel | 40 mg |
| Glycerol | 500 mg |
| TWEEN ® 80 | 1500 mg |
| Deoxycholic acid | 400 mg |
| Mannitol | 600 mg |
| WFI water | Add to 10 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 16

| | |
|---|---|
| Docetaxel | 20 mg |
| Glycerol | 300 mg |
| TWEEN ® 80 | 550 mg |
| Sodium Glycocholate | 200 mg |
| Mannitol | 300 mg |
| WFI water | Add to 5 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

EXAMPLE 17

| Docetaxel | 20 mg |
|---|---|
| Polyethylene glycol 400 | 350 mg |
| TWEEN ® 80 | 1000 mg |
| Sodium taurocholate | 400 mg |
| Mannitol | 400 mg |
| WFI water | Add to 6 mL total volume |

The injection solution of this example was prepared using the procedure described in example 1. The amounts and compounds used were as in the table above.

Turbidity of the injection solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of this example is less turbid than that of the reference solution of scale No. 1, rated "clear".

Procedures of Preparing Powder for Injection

The solutions prepared in Example 1-17 were lyophilized using the following procedure:
the sample was pre-frozen at −45° C. for 3 hours before sublimation; the temperature of the lyophilization was maintained at −12° C.;
the second stage drying process was carried out at 35° C. until the weight loss met the requirement;
the vials containing dry powder were caped inside a drying chamber and further sealed with aluminum foil outside the chamber;
the sample vials further underwent quality control and packaging.

Turbidity Test of the Freeze-Dried Powder

Between 3 mL and 15 mL of water was injected into a vial to dissolve the dry powder and the turbidity of the solution was measured following the procedures published in "Chinese Pharmacopoeia 2005 (2)" Appendix IX B. Both sample solution and standard solutions were freshly prepared and placed in Nessler tubes with equal volumes. The solutions were allowed to stand for 5 min before the measurement. The tubes were placed vertically under umbrella light with light intensity of 1000 Lux in a dark room. Turbidity was observed from the side and the sample solution of example solution is less turbid than that of the reference solution of scale No. 1, rated "clear". The solution maintained its clarity after standing at room temperature for eight hours.

Conventional Examples for Comparison

Composition 1: Glycerol as the Only Surfactant/Primary Solvent

| Docetaxel | 20 mg |
|---|---|
| Glycerol | 800 mg |
| WFI water | 4 mL |

The test has shown that docetaxel does not dissolve in the mixture of glycerol and water in this particular formulation. No clear solution was obtainable for pre-frozen powder. The sample after lyophilization was mixed with 10 mL of WFI water and the mixture was tested for turbidity. The sample was rated "turbid" based on the method described above.

Composition 2: TWEEN® as the Only Surfactant/Primary Solvent

| Docetaxel | 20 mg |
|---|---|
| TWEEN ® 80 | 700 mg |
| WFI water | 4 mL |

The test has shown that docetaxel does not dissolve in the mixture of TWEEN® 80 and water. No clear solution was obtainable for pre-frozen powder. The sample was mixed with 10 mL of WFI water after lyophilization and the mixture was tested for turbidity. The sample was rated "turbid" based on the method described above.

Composition 3: Polyethylene Glycol as the Only Surfactant/Primary Solvent

| Docetaxel | 20 mg |
|---|---|
| Polyethylene glycol 400 | 400 mg |
| WFI water | 4 mL |

The test has shown that docetaxel does not dissolve in the mixture of polyethylene glycol 400 and water. No clear solution was obtainable for pre-frozen. The sample was mixed with 10 mL of WFI water after lyophilization and the mixture was tested for turbidity. The sample was rated "turbid" based on the method described above.

The foregoing examples demonstrate that the solubility of docetaxel is significantly, yet unexpectedly, improved by using the mixture of TWEEN® and a solubilizing agent. When used alone, neither TWEEN®, nor glycerol, nor polyethylene glycol, increase the solubility of docetaxel in aqueous solution.

EXAMPLE 18

Stability Study Under Accelerated Conditions

Freeze-dried powders prepared in Example 1-17 have the desired advantages as described herein. These advantages, properties and the composition of the components do not change after 6 months of storage under accelerated experimental conditions. The content of the active ingredient remain between 98% and 101.05% and the changes of contents of other additives were less than 0.8%. That was well within an acceptable range. Per these results, the freeze-dried compositions are expected to have an effective shelf life of two years.

EXAMPLE 19

Hypersensitive Reaction/Irritation Study

The powder samples made as described in Examples 1-4, 6-7, 10, and 11-17 were tested in animals to examine the reaction and tolerance. Specifically, six healthy domestic rabbits, were randomly grouped into two according to the body weight. One group was given docetaxel composition using IV injection through a vein on the left ear and the dose was designed to be proportional to that normally given to a human adult. The control group was given saline of the same volume as that of docetaxel injection in the other group. The intravenous administration was continued for 5 days. The animals were carefully examined and compared during the administration period and 24 hours after the last injection.

There was no irritation or inflammation on blood vessel or the area around injection based on eye observation. The histological section of the rabbit's ear showed that veins were normal with dilations on one or two blood vessel. The thickness of the vessel wall appeared even and the inner wall looked smooth with no signs of inflammation. These results indicate that the injection of the docetaxel composition does not cause vascular irritation to the rabbit's veins.

What is claimed is:

1. A pharmaceutical composition comprising:
   a) between 1 mg/mL and 80 mg/mL docetaxel;
   b) between 20 mg/mL and 500 mg/mL of a polysorbate surfactant selected from the group consisting of polysorbate 20, polysorbate 40, polysorbate 60, polysorbate 80, and mixtures thereof; and
   c) between 5 mg//mL and 500 mg/mL of a solubilizing agent selected from the group consisting of glycerol, polyethylene glycol, and mixtures thereof;
   wherein
   said pharmaceutical composition does not comprise ethanol;
   wherein the weight ratio of docetaxel to said polysorbate surfactant to said solubilizing agent is 1:10-80:5-50; and
   wherein said pharmaceutical composition forms a clear solution when mixed with water.

2. The composition of claim 1, wherein the weight ratio of docetaxel to said polysorbate surfactant to said solubilizing agent is 1:25-40:10-30.

3. The composition of claim 1, wherein said surfactant is polysorbate 80.

4. The composition of claim 1, wherein said solubilizing agent is glycerol.

5. The composition of claim 1, wherein the solubilizing agent is polyethylene glycol.

6. The composition of claim 5, wherein said polyethylene glycol is polyethylene glycol 200, polyethylene glycol 400, polyethylene glycol 800, or a mixture thereof.

7. The composition of claim 6, wherein said polyethylene glycol is polyethylene glycol 400.

8. The composition of claim 1, wherein the composition further comprises one or more pharmaceutically acceptable additives.

9. The composition of claim 1, wherein the composition further comprises a bile acid or a salt thereof.

10. The composition of claim 9, wherein said bile acid is a free bile acid, a conjugated bile acid, or the mixture thereof, and the salt is a metal salt, and said conjugated bile acid is a conjugate of a bile acid with glycine or taurine.

11. The composition of claim 10, wherein said free bile acid is cholic acid, lithocholic acid, deoxycholic acid, chenodeoxycholic acid, ursodeoxycholic acid, hyodeoxycholic acid, or a mixture thereof.

12. The composition of claim 11, wherein said free bile acid is cholic acid, deoxycholic acid, chenodeoxycholic acid, ursodeoxycholic acid, hyodeoxycholic acid, or a mixture thereof; and said conjugated bile acid is glycocholic acid, glycodeoxycholate, glycochenodeoxycholic acid, glycoursodeoxycholic acid, glycohyodeoxycholic acid, taurocholic acid, taurodeoxycholic acid, taurochenodeoxycholic acid, tauroursodeoxycholic acid, taurohyodeoxycholic acid, or a mixture thereof.

13. The composition of claim 10, wherein said bile salt is a potassium salt, a sodium salt, a calcium salt, a magnesium salt, a zinc salt, or a selenium salt of said bile acid.

14. A method of treating a cancer comprising administering to a patient the pharmaceutical composition of claim 1.

15. The method of claim 14, wherein the cancer is primary cancer or metastatic cancer selected from breast cancer, non-small cell lung cancer, small cell lung cancer, ovarian cancer, AIDS-related Kaposi's sarcoma, pancreatic cancer, colorectal cancer, melanoma, head and neck cancer, lymphoma, brain tumor, or gastric cancer.

16. A method of manufacturing the composition of claim 1, comprising mixing docetaxel, a solubilizing agent, and a polysorbate surfactant; and freeze-drying.

17. The method of claim 16, comprising mixing docetaxel, a polysorbate surfactant, a solubilizing agent, and cholic acid or a salt thereof.

18. The method of claim 16, further comprising adding activated carbon, filtering off the activated carbon, and removal of microbes, said adding activated carbon, filtering off the activated carbon, and removal of microbes being performed after said mixing of docetaxel, a solubilizing agent, and a polysorbate surfactant and before said freeze-drying.

19. The composition of claim 1 provided in a form suitable for parenteral administration.

20. The composition of claim 1, wherein said surfactant is polysorbate 80, and said solubilizing agent is a mixture of polyethylene glycol 400 and glycerol.

21. The method of claim 16, wherein the method does not comprise admixing or removing ethanol at any point during manufacturing of the composition.

22. A pharmaceutical composition comprising an aqueous solution of:
   a) between 1 mg/mL and 80 mg/mL docetaxel;
   b) between 20 mg/mL and 500 mg/mL of a polysorbate surfactant selected from the group consisting of polysorbate 20, polysorbate 40, polysorbate 60, polysorbate 80, and mixtures thereof; and
   c) between 5 mg//mL and 500 mg/mL of a solubilizing agent selected from the group consisting of glycerol, polyethylene glycol, and mixtures thereof;
   wherein
   said pharmaceutical composition does not comprise ethanol;
   said pharmaceutical composition is clear and does not comprise any solid particles; and
   wherein the weight ratio of docetaxel to said polysorbate surfactant to said solubilizing agent is 1:10-80:5-50.

* * * * *